US012210498B1

(12) United States Patent
Case et al.

(10) Patent No.: US 12,210,498 B1
(45) Date of Patent: *Jan. 28, 2025

(54) SYSTEM AND METHOD FOR AUTOMATED CLUSTERING OF SUBJECT DATA

(71) Applicant: Verato, Inc., McLean, VA (US)

(72) Inventors: Jonathan Paul Case, Cary, NC (US); Carl Hecker, Annandale, VA (US); Luis Vicente Orozco, Vienne, VA (US); Tara Fachada Figley, Morrisville, NC (US); Sean Michael Pritchard, Clayton, NC (US)

(73) Assignee: Verato, Inc., McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/393,926

(22) Filed: Dec. 22, 2023

Related U.S. Application Data

(63) Continuation of application No. 16/807,854, filed on Mar. 3, 2020, now Pat. No. 11,907,187, which is a continuation-in-part of application No. 15/581,956, filed on Apr. 28, 2017, now Pat. No. 11,899,632.

(51) Int. Cl.
| | | |
|---|---|---|
| *G06F 16/215* | (2019.01) | |
| *G06F 16/27* | (2019.01) | |
| *G06F 21/62* | (2013.01) | |

(52) U.S. Cl.
CPC ............ *G06F 16/215* (2019.01); *G06F 16/27* (2019.01); *G06F 21/6254* (2013.01)

(58) Field of Classification Search
CPC ..... G06F 21/6254; G06F 16/27; G06F 16/215
See application file for complete search history.

(56) References Cited

U.S. PATENT DOCUMENTS

| | | |
|---|---|---|
| 6,389,429 B1 | 5/2002 | Kane et al. |
| 7,046,994 B1 | 5/2006 | Padawer et al. |
| 7,209,911 B2 | 4/2007 | Boothby et al. |
| 7,363,325 B2 | 4/2008 | Yianilos et al. |
| 7,509,326 B2 | 3/2009 | Krabel et al. |

(Continued)

OTHER PUBLICATIONS

Phatak, et al., Conflict Resolution and Reconciliation in Disconnected Databases; Department of Computer Science, Rutgers University, New Brunswick, NJ; pp. 1-6.

(Continued)

*Primary Examiner* — Hosain T Alam
*Assistant Examiner* — Anthony G Gemignani
(74) *Attorney, Agent, or Firm* — Fox Rothschild LLP

(57) ABSTRACT

A method and system for detecting and queuing data stewardship tasks, the method may comprise receiving, at a private database, incoming identity information comprising one or more received data record attributes; comparing the one or more received data record attributes to a plurality of saved data records in the private database. Each saved private data record may include one or more saved attributes. A data stewardship task record is created that contains the received data record attributes and saved data record attributes that are near matches to the received data record. The data stewardship task is displayed to indicate a match quality for each of the received data record attributes and the saved data record attributes. The match quality may be indicated using a color coding scheme that uses a unique color or lack of color to indicate one of a match, a partial match, and no match.

21 Claims, 11 Drawing Sheets

(56) References Cited

U.S. PATENT DOCUMENTS

| | | |
|---|---|---|
| 7,546,286 B2 | 6/2009 | Dickinson et al. |
| 7,627,611 B2 | 12/2009 | Gusciora |
| 7,707,177 B2 | 4/2010 | Bank et al. |
| 7,788,225 B2 | 8/2010 | Fish et al. |
| 8,001,078 B2 | 8/2011 | Banks et al. |
| 8,301,593 B2 | 10/2012 | Hoffmann et al. |
| 8,589,510 B2 | 11/2013 | Jackson |
| 8,892,571 B2 | 11/2014 | Friedlander et al. |
| 9,129,046 B2 | 9/2015 | Bess et al. |
| 9,195,725 B2 | 11/2015 | Brown et al. |
| 9,286,369 B2 | 3/2016 | Pei et al. |
| 9,519,798 B2 | 12/2016 | Egorov et al. |
| 9,892,231 B2 | 2/2018 | Vdovjak |
| 10,249,385 B1 | 4/2019 | McNair et al. |
| 10,340,033 B2 | 7/2019 | Bucur et al. |
| 10,657,613 B2 | 5/2020 | Bucur et al. |
| 11,114,185 B1 | 9/2021 | Malec et al. |
| 2003/0055828 A1 | 3/2003 | Koch et al. |
| 2004/0148290 A1 | 7/2004 | Merenda et al. |
| 2005/0240569 A1 | 10/2005 | Cheng et al. |
| 2006/0123010 A1 | 6/2006 | Landry et al. |
| 2006/0271401 A1 | 11/2006 | Lassetter et al. |
| 2008/0208797 A1 | 8/2008 | Witzke et al. |
| 2009/0210453 A1 | 8/2009 | Vetter et al. |
| 2010/0169348 A1 | 7/2010 | Maro et al. |
| 2010/0312766 A1 | 12/2010 | Horn |
| 2011/0039249 A1 | 2/2011 | Packard et al. |
| 2011/0066446 A1 | 3/2011 | Malec et al. |
| 2011/0246237 A1 | 10/2011 | Vdovjak |
| 2012/0158807 A1 | 6/2012 | Woody et al. |
| 2012/0233209 A1 | 9/2012 | Cheng et al. |
| 2012/0233530 A1 | 9/2012 | Stroe et al. |
| 2014/0040313 A1 | 2/2014 | Shami et al. |
| 2014/0136440 A1 | 5/2014 | Ahmed et al. |
| 2015/0025913 A1 | 1/2015 | Friedlander et al. |
| 2015/0149488 A1 | 5/2015 | Ebaugh et al. |
| 2015/0213380 A1 | 7/2015 | Cooper et al. |

OTHER PUBLICATIONS

Eze et al., "A Patient Identity Matching Service for Cloud-based Performance Managemenet of Community Healthcare," Procedia Computer Science (2017); 113: 287-294.

Sauleau et al., "Medical record linkage in health information systems by approximate string matching and clustering," BMC Medical Informatics and Decision Making (2005); 5(32): 1-13.

Khan et al., "Similarity Analysis of Patients' Data: Bangladesh Perspective," International Conference on Medical Engineering, Health Informatics and Technology (2016): 1-5.

Verato, Inc., "Verato Link," Verato Identity Integrity, 2015 (2 pages).

Verato, Inc., "Verato Validate," Verato Identity Integrity, 2015 (2 pages).

Verato, Inc., "Verato Linktm," Verato Identity Integrity, 2015 (2 pages).

Verato, Inc., "Verato Validatetm," Verato Identity Integrity, 2015 (2 pages).

| | Source ∨ | Type ∨ | Status ∨ | ⊙ To. From ⊙ | Assignee ∨ | Match score ∨ |
|---|---|---|---|---|---|---|
| 5c9cedd1995af3800086a2651 | test, TST1 | Multiple reference IDs | In progress | 01/01/2018 14:01 | Rob Smith | 0.71 |
| 5c9cedd1995af3100086a2651 | tu, TST21 | Multiple reference IDs | In progress | 01/01/2018 14:01 | Noah Cyrus | 0.72 |
| 5c9cedd1995af2800086a2651 | test, TST2 | Multiple reference IDs | In progress | 01/01/2018 14:01 | Ravi Singh | 0.712 |
| 5c9cedd1995af3800086a2651 | test, TST3 | Multiple reference IDs | In progress | 01/01/2018 14:01 | Bob Smith | 0.713 |
| 5c9cedd1995af3800086a2651 | test, TST4 | Potential match - same source | In progress | 01/01/2018 14:01 | Will Smith | 0.73 |
| 5c9cedd1995af3800086a2651 | test, TST5 | Multiple reference IDs | In progress | Today 14:01 | John Taylor | 0.745 |
| 5c9cedd1995af3800086a2651 | test, TST6 | Potential match - cross source | Resolved | 01/01/2018 14:01 | Jacob | 0.71 |
| 5c9cedd1995af3800086a2651 | test, TST7 | Multiple reference IDs | In progress | 01/01/2018 14:01 | Peter Parker | 0.72 |
| 5c9cedd1995af3800086a2651 | test, TST8 | Multiple reference IDs | In progress | 01/01/2018 14:01 | Kate Hudson | 0.713 |
| 5c9cedd1995af3800086a2651 | test, TST9 | Multiple reference IDs | In progress | 01/01/2018 14:01 | Sai K | 0.781 |
| 5c9cedd1995af3800086a2651 | test, TST0 | Multiple reference IDs | Resolved | 01/01/2018 14:01 | Benjamin Franklin | 0.79 |
| 5c9cedd1995af3800086a2651 | tu, TST1 | Multiple reference IDs | Resolved | 01/01/2018 14:01 | Mickey Mouse | 0.713 |
| 5c9cedd1995af3020086a2651 | tu, TST2 | Multiple reference IDs | Resolved | 01/01/2018 14:01 | Christopher | 0.711 |
| 5c9cedd1995af3800086a2651 | tu, TST3 | Multiple reference IDs | Open | 01/01/2018 14:01 | Richard | 0.71 |

FIG. 6

| Link ID: 5ba3525757b272a3b6d5 | | | | | | | |
|---|---|---|---|---|---|---|---|
| Source | Native ID | Gender | First Name | Middle Name | Last Name | SSN | DOB | Address Line 1 |
| a | 1 | M | ROBERT | ADAM | JONES | | 1993-04-16 | 123 MAIN ST |
| | | | | | | | | 46 HALSTED AVE |
| b | 200 | M | ROBERT | ADAM | JONES | 000000000 | 1993-04-16 | 878 ELM ST |
| c | 9000 | M | ROBERT | ADAM | JONES | 323445656 | 1995-04-16 | 46 HALSTED AVE |

Reference Identity

| | | | ROBERT | ADAM | JONES | | 1993-04-16 | 878 ELM ST |
| | | | | | | | | 46 HALSTED AVE |

701

| Link ID: 5be45df4783.1de073f0c9f54 | | | | | | | |
|---|---|---|---|---|---|---|---|
| Source | Native ID | Gender | First Name | Middle Name | Last Name | SSN | DOB | Address Line 1 |
| d | 4321 | M | BUZZ | | JONES | | 1993-04-16 | 123 MAIN ST |

SYSTEM AND METHOD FOR AUTOMATED CLUSTERING OF SUBJECT DATA

RELATED APPLICATIONS AND CLAIM OF PRIORITY

This application claims priority to and is a continuation of U.S. patent application Ser. No. 16/807,854 which was a continuation-in-part of U.S. patent application Ser. No. 15/581,956, the contents of both of which are hereby incorporated by reference in their entirety.

FIELD OF THE DISCLOSURE

This invention relates to the field of information sharing among computer systems, specifically real-time, Web services, and/or batch interactions that are conducted between two or more systems within a single heterogeneous enterprise, or are conducted between two or more systems across two or more heterogeneous enterprises, and graphical user interfaces useful for matching and linking data records pertaining to a given subject despite variations in the attributes used in different systems and enterprises to describe that subject.

BACKGROUND

Currently, when a record containing attributes that pertain to a given person or entity (i.e., the subject) are presented to a data system for use in a given process, that data system employs a matching algorithm to determine whether or not the data system's database contains a corresponding record. Depending on the type of matching algorithm used to compare the attributes contained in the presented record from a first system, to the records in a second database associated with a second system, there are several outcomes that could occur. For example, if all the attributes pertaining to the subject contained in the presented record match the attributes contained in the second database, the matching algorithm(s) might conclude that the data transaction pertaining to the subject can be processed. However, and by way of example only, if the matching algorithms determine there is not a match between the presented record and the second database, such a determination might incorrectly result in a false negative. Such a scenario could result in the data transaction being incorrectly rejected; or possibly incorrectly creating duplicate records for the same subject. Alternatively, the matching algorithms might incorrectly determine that the attributes do match and thus identify the subject in both the presented record and in the second database as one and the same, when in fact the two subjects are not the same person or entity, resulting in a false positive.

SUMMARY OF THE INVENTION

Methods, systems, and devices that enable data stewardship tasks for linking and unlinking internal records associated with subjects, across disparate enterprises, on an enduring basis when the subjects are identified by attributes, are disclosed.

A method and system for detecting and queuing data stewardship tasks, the method may comprise receiving, at a private database, incoming identity information comprising one or more received data record attributes; comparing the one or more received data record attributes to a plurality of saved private data records in the private database, wherein each saved private data record comprises one or more saved private data record attributes; on a condition that the received data record is a near match to one or more of the plurality of saved private data records in the private database, creating a data stewardship task record that contains the one or more received data record attributes and the one or more saved private data record attributes of each of the plurality of saved private data records that are near matches to the received data record; and displaying a data stewardship task on a display, wherein the displayed data stewardship task indicates a match quality for each of the one or more received data record attributes and the saved private data record attributes. The match quality may be indicated using a color coding scheme that uses a unique color, lack of color, or some other visual cues, to indicate a match, a partial match, and no match.

The method may also comprise receiving a first user input indicating one of a linking action or an unlinking action, wherein the first user input indicates a linking action and wherein the first user input includes a reference to an identified saved private data record included in the data stewardship task, and assigning the received data record a private record identifier of the identified saved private data record. And if the first user input indicates an unlinking action and wherein the first user input includes a reference to an identified saved private data record included in the data stewardship task, the method further comprising assigning the identified saved private data record a new private identifier and saving the identified saved private data record as a new private data record.

The method also may comprise, prior to creating the data stewardship task, assigning a new private identifier to the received data record and saving the received data record as a new private data record.

The method may also comprise, prior to creating the data stewardship task, on a condition that a currently existing data stewardship tasks contain a previously received data record is a near match to the one or more of the plurality of saved private data records in the private database, merging the received data record into the currently existing data stewardship task.

The method may also comprise comparing the one or more received data record attributes to a plurality of saved reference data records in a reference database that is in communication with the private database, wherein each saved reference data record comprises one or more saved reference data record attributes and, on a condition that the received data record is a near match to one or more of the plurality of saved reference data records in the reference database, creating a data stewardship task record that contains the one or more received data record attributes and the one or more saved reference data record attributes of each of the plurality of reference data records that are near matches to the received data record. The displayed data stewardship task may also indicate a match quality for each of the one or more received data record attributes and the saved reference data record attributes.

A system for viewing and performing data stewardship tasks may include a private data system that includes a private database, wherein said private database contains one or more private data records, each pertaining to a subject, that are each associated with one or more private attributes, wherein one of such private attributes for each private data record is a private data record identifier (ID) attribute, and wherein said private database includes all private attributes regarding private data records contained in said private data system; a reference data system that includes a reference database, wherein each reference data record in the reference database pertains to a subject and is comprised of reference data attributes associated with the subject, and each reference data record contains a reference record identifier attribute.

BRIEF DESCRIPTION OF THE DRAWINGS

FIG. 6 is an example graphical user interface for use in implementing the disclosed embodiments.

FIGS. 7A-7C are an example graphical user interface for use in implementing the disclosed embodiments.

DETAILED DESCRIPTION OF THE PREFERRED EMBODIMENTS

Figure 1:
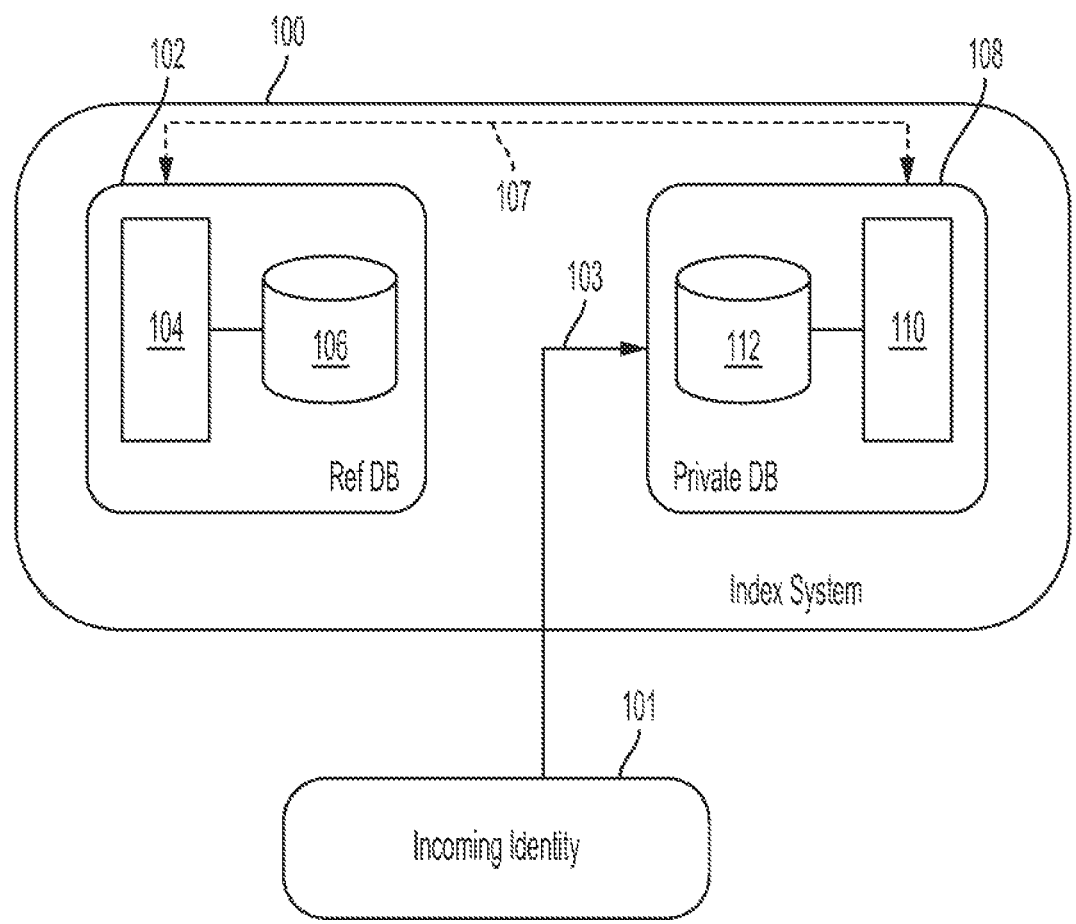
FIG. 1 is a block diagram showing example data systems for use in implementing the disclosed embodiments.

Embodiments of the present invention are not limited to the particular methodology, uses, and applications described herein, as these may vary. It is also to be understood that the terminology used herein is used for the purpose of describing particular embodiments only, and is not intended to limit the scope of all embodiments of the present invention. It must be noted that as used herein and in the appended claims, the singular forms "a," "an," and "the" include the plural reference unless the context clearly dictates otherwise. Thus, for example, a reference to "an element" is a reference to one or more elements, and includes equivalents thereof known to those skilled in the art. Similarly, for another example, a reference to "a step" or "a means" is a reference to one or more steps or means and may include sub-steps or subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Reference will now be made in detail to the preferred embodiments of the invention, examples of which are illustrated in the accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art.

Unless defined otherwise, all technical and scientific terms used herein have the same meanings as commonly understood by one of ordinary skill in the art to which this invention belongs. Preferred methods, techniques, devices and materials are described although any methods, techniques, devices, or materials similar or equivalent to those described may be used in the practice or testing of the present invention.

All patents and other publications discussed are incorporated herein by reference for the purpose of describing and disclosing, for example, the methodologies described in such publications that might be useful in connection with the present invention. These publications are provided solely for their disclosure prior to the filing date of the present application. Nothing in this regard should be construed as an admission that the inventors are not entitled to antedate or otherwise remove any such publication or patent as prior art for any reason.

As used in this document, a subject of a data record is the person, individual, group, entity, or thing (whether tangible or intangible) that the data record pertains to. For example, in the context of health data systems, a subject may be a patient or insurance policy holder. Alternatively, in this example, the subject may also be a doctor, hospital, or insurance company.

As used in this document, the term "associate uniquely", "associates uniquely", and similar variants means, with regard to data records in a data system, that the subject of a particular data record is uniquely identified to be the same as the subject of another data record (or query) because the attributes in one record can be shown to be representative of the subject of the other record through a given matching technique or a combination thereof, despite variations in the attributes, and to the exclusion of all other subjects represented by the attributes stored in their data records.

As used in this document, the term "private" means a service or system that is provided for exclusive use by an enterprise or a group of enterprises and is not directly accessible over a public network by other enterprises. As used in this document, the phrase "private database" means a database provided to an enterprise or group of enterprises for the exclusive use by that enterprise or group of enterprises. A "private data system" is a data system that includes a private database and also includes a processor and other hardware and software elements used to implement the methods disclosed below.

As used in this document, the term "reference database" means a database provided to any enterprise or group of enterprises that subscribes to or otherwise has access to the database. The reference database is intended to be a comprehensive database of all known or nearly-all known or publicly available or purchasable data regarding subjects as discussed herein, and could include by way of example only persons within a country, state, region, or other political subdivision. A "reference data system" is a data system that includes a reference database and other hardware and software elements used to implement the methods disclosed below.

As used in this document, the term "private attribute" or "private attributes" means one or more attributes that are stored in a private database for the private use of the enterprises who have access to the private data system. Private attributes are stored such that they cannot be accessed by systems or processes that have access to the reference data system unless they are permitted by the enterprise from which the private attributes are provided.

As used in this document, the term "source ID" means an identifier of the source of a particular data record, and "source record" means a data record that originated from the source identified by the source ID. For example, all records that have the same source identifier ("ID") may have all originated from the same source identified by that source ID. In this example, a source record is a data record that contains a set of attributes that can be used to identify the subject of the source record. Included in the source record and/or source ID is a unique identifier, or native ID, that represents the subject in the source database. The source ID and native ID may be stored in the private database to indicate the origin of the record, for example. In an embodiment, the source ID includes both an indicator of source and the native ID (Source+Native ID) of the subject in that source database.

It would be advantageous to have an index system that provides an interactive, possibly cloud-based matching and linking capability that connects subject records across disparate private and public systems within and across enterprises. Such an index system may, for example, use a referential matching approach, which finds matching subject records based on both the data values in private subject records themselves as well as a comprehensive public reference database of subjects. Each unique subject found within private subject records may be assigned a unique identifier, called a private identifier ("ID"). More than one private subject record may be assigned the same private ID, for example, whenever those subject identity records are deemed to be the same subject based on, for example, referential matching using the public reference database.

Similarly, it would be advantageous to accurately identify where the same subject identity exists in records within and across multiple data systems in an enterprise. The assigned private ID can be used within the enterprises analytical or operational processes, or users can interactively query a graphical user interface ("GUI") of the index system to find a unique subject on demand.

It would also be advantageous to enable users to manually change or 'override' the matching and linking decisions made by the index system, thereby allowing the user to choose to alter the automated assignment of which source records are assigned to each private ID (i.e., manually select which source records are associated with the same subject assigned to a given private ID). This activity is referred to as 'data stewardship'. To facilitate these manual data stewardship decisions, the aforementioned GUI is provided. Using the GUI, users can retrieve and view identity records from the index system, or as applicable, the index system instance in a cloud configuration. If a user decides that a set of source records within one or more private IDs should be linked together (or split apart), the user can take this action using the GUI.

Using the GUI, users may take one of two actions to alter the grouping of source records within a private ID: link identities and unlinking source records. When a user links identities, they select a first private ID (which includes all source records assigned to that private ID) and combine the first private ID with a second private ID. The first private ID is 'linked into' the second private ID and the source records all become assigned to the second, surviving, private ID, indicating they all represent one person (i.e., a single subject). When a user unlinks one or more source records, they select a subset of source records within a private ID and split those selected source records out into one or more new private IDs, indicating they represent one or more different subjects. Users may use combinations of linking and unlinking to apply more sophisticated changes to the overall assignment of private IDs for a set of source records, but the fundamental specific actions taken by the user in the GUI are linking identities and unlinking source records.

The GUI enables data stewards to view and link or unlink source records in two different modes: search mode and task mode. In search mode, a user may search and retrieve any subject records in the index system through a demographic search or ID lookup. Subject records retrieved in search mode are viewed in a 'workspace', which can contain as many identities as the user wants to retrieve and view. From the 'workspace', the user may link identities and unlink source records. In task mode, the index system may proactively detect and queue up data stewardship 'tasks' for the user to view, based on conditions present in the data at the time the source records were posted to the index system. For example, the index system may detect and queue up the following categories of tasks. First, the index system may detect near matches within the same source. If multiple source records from the same source are posted over time with similar demographic data values that do not automatically match and link together via any input matching algorithm or the like, the index system may mark them as a data stewardship task that users may be interested in reviewing. A data stewardship task in the category of "Potential Match-Same Source" may contain identities made up of source records from several sources, but it will contain at least two different identities (each with a different private ID) with source records from the same source. Second, the index system may detect near matches across different sources. If multiple source records from different sources are posted over time with similar demographic data values that do not automatically match and link together via any input matching algorithm or the like, the index system may mark them as data stewardship tasks that users may be interested in reviewing. A data stewardship task in the category of "Potential Match-Cross Source" may occur when the posted source record is a near match to other identities that do not contain any source records from the same source as the posted source record. Index system GUI users may navigate between the search and task modes. The search mode, task mode, and navigation options are described in more detail below.

In an example implementation, shown in FIG. 1, incoming identity data records 101 can be, for example, posted into index system 100. The index system may comprise, for example, a reference data system 102 and a private data system 108. Reference data system 102 includes a reference processor 104 and a reference database 106. The data records in the reference database 106 may include, for example, a reference ID (i.e., a unique identifier), and reference demographic attributes, for example, personally-identifying information associated with the subject identity, such as name, address, birth date, SSN, and phone number. Similarly, private data system 108 includes private processor 110 and private database 112. Private database 112 may include, for example, a customer ID (i.e., a unique identifier within the private database), customer demographics, for example personally-identifying information associated with the identity, such as name, address, birth date, SSN, and phone number, a reference ID (i.e., a unique identifier for a matching identity record in the reference database 106), and a private ID (i.e., a unique identifier to identify a unique person within the index system). As an example, if the index system matches customer demographics of a private data record with reference demographics of a reference data record, the reference ID is stored in the private database 112 for future matching purposes. As another example, if multiple private data records are determined by the index system to match the same unique identity, each of the multiple private data records may be assigned the same private ID in the private database 112 to indicate they belong to the same subject. A person of ordinary skill will understand that the depiction of FIG. 1 is a logical diagram and index system 100 and its various components may be independently or otherwise maintained on a single server, multiple server or server farm, or in a cloud configuration either by a single entity or by multiple entities in collaboration. The embodiments of the present disclosure are not limited in this regard.

Alternative embodiments of index system and other uses of private and reference data systems are described in greater detail in U.S. patent application Ser. No. 15/581,956, filed on Apr. 28, 2017, the entire disclosure of which is hereby fully incorporated by reference in its entirety as if fully set forth herein.

To use the index system, a user may log-in to a typical log-in page with username and password fields among other features that are well-known in the art. Upon authentication, a user may choose to each conduct a search or view a task. A form or other user interface feature enables a user to perform a search or retrieve specific identities of their choosing. The search mode features multiple options for retrieving identities. One of the options to retrieve identities in the user interface is to retrieve the private identity associated with a specific combination of private attributes known to identify a single subject, for example, a source ID and native ID. Another option to retrieve identities in the user interface is to retrieve the reference identity by private ID, the unique ID assigned to each identity in the private database. A third option to retrieve identities in the user interface is to search for subject identities by demographics, such as name, birth date, address, and so on. The demographics search option also allows you to search for identities matching one or more 'extended' demographic attributes such as combination identifiers, for example, unique identifiers created from combinations of other attributes, or alternate identifiers associated with a particular subject. A person of ordinary skill would understand that the universe of values or data points usable as demographic attributes is not limited in any way. By default, for example, the prompt may start with an option to search by demographic attribute values.

Once a search is run, using any of the above described options or any other known technique, a search results screen may appear if the search returned results. If no results are returned, a warning or other method of communicating the lack of results may be issued. In the search results view, the demographic search input fields may be displayed across the top row of the page (still showing the input fields you entered) while the retrieved identities may displayed in rows below. For example, the search for 'Alan Peoples' at the address '123 Main St, Chicago IL' may return two identities.

Each identity row displayed in the search results, in an example, may correspond to a single distinct private ID. This private data record associated with the private ID may be comprised of one or many source records, but in the initial search results view each private ID may be collapsed into a single row, representing a single unique person, for example. Each matching identity is assigned a numeric score, indicating the similarity between the input demographic search data and the attribute data on the identity record(s). The scores, for example, may range from 0.0 to 1.0, with 0.0 representing zero similarity between the search input and the identity record and 1.0 representing the highest level of similarity between the search input and the identity record, for example. Search results with a lower score, for example, may have less in common with the input values. In a specific example, the first search result may have a 0.74 score, based on similarity in the name and address values; the second search result may have a lower score of 0.56 because it had less data in common (last name and address matched, but not first name, for example).

The search results displayed to the user may include many different identities from the index system, not all of which are interesting to the user. After reviewing the search results, the user can select one or more search results to work with in the 'Workspace' view. The Workspace view, for example, may be a view from which a user can make linking and unlinking decisions, described in more detail below in reference to FIGS. 7A, 7B, and 7C.

When an identity is retrieved, for example, by either its private ID or source ID (i.e., Source+Native ID), the user is shown the entire identity in the Workspace view of the GUI. When a user searches for identities by demographics, the user may select which identities to view in the Workspace. The subject identity is made up of (a) one or more source records that have been assigned to the same private ID because they are deemed to be the same subject, and (b) the reference identity for that subject, if the source records definitively matched to a reference identity. Note that in the case of retrieving an identity by its source ID, the identity may be made up of additional source records with other Source+Native ID combinations (i.e., all the source records that are associated with the particular private ID).

Figure 2:
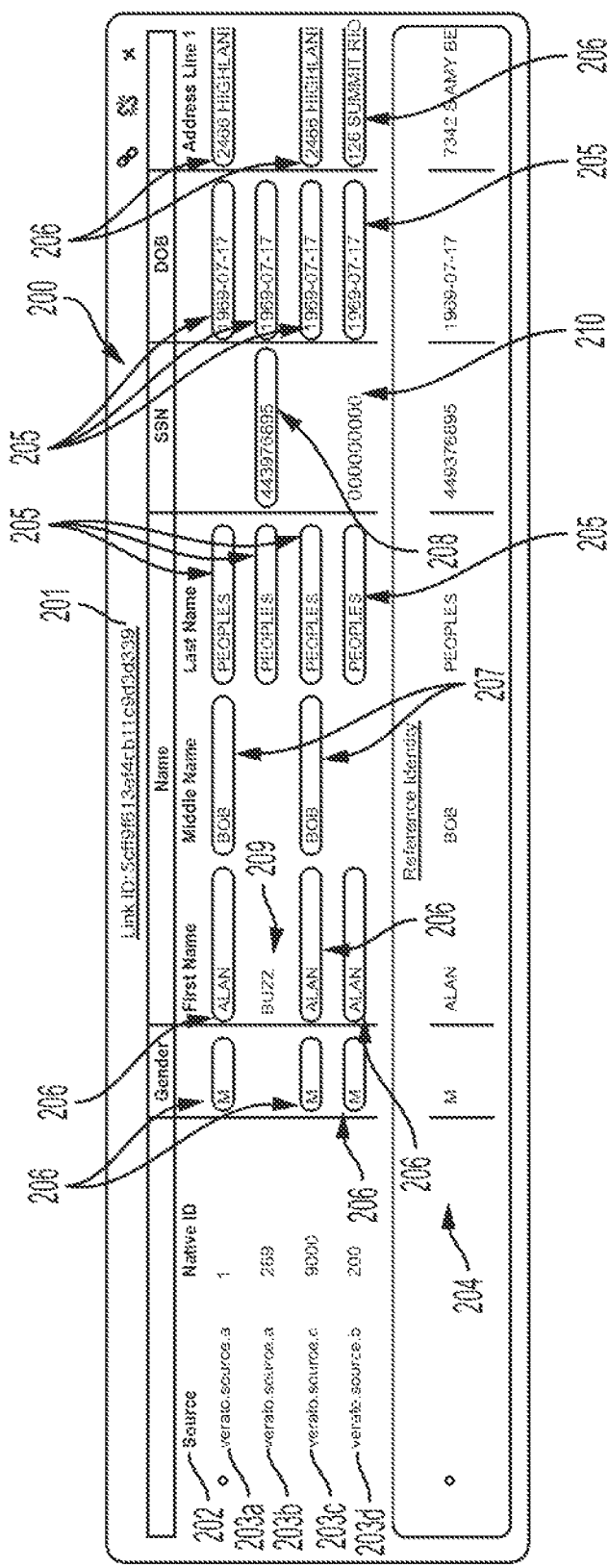
FIG. 2 is an example graphical user interface for use in implementing the disclosed embodiments.

Referring to FIG. 2, an embodiment of a workspace is shown. All the data associated with the identity is grouped together in workspace 200 surrounded by a bold outline. The private ID 201 (in this embodiment referred to as a "Link ID") assigned to the identity being viewed is displayed at the top of the grouping of data. Below the private ID 201 is a header row 202 indicating the data value populated in each column (for example, Source, Native ID, First Name, Last Name, and so on). Each source record 203a, 203b, 203c, 203d is displayed as a single row with, for example, one name, one address, one birth date, and so on. The reference identity 204, if one was matched to the source records 203a-d, is displayed at the bottom of the grouping of data shaded in gray with a non-bold outline. If no reference identity was matched to the source records, for example, the user will not see any gray-shaded identity data, only the located source records.

When an identity is retrieved whose source records have matched a reference identity record, the GUI, for example, uses green and yellow (or other color) shading to indicate the source record data similarity to the reference data in the reference identity record. Each source record attribute value that matches data from the reference identity record is highlighted in green or other color. Each source record attribute value that partially matches data from the reference identity record is highlighted in yellow or other color. A partial match is any match other than an exact match. For example, a partial match may include abbreviated or truncated names, such as "Al" or "Bert" for "Albert". A partial match may also include, for example, common nicknames such as "Chuck" for "Charles" and "Peggy" for "Margaret", and the like. Such "fuzzy" partial matching can extend to misspellings and character transpositions as well, enabling address fields "23 Charter Lane" and "32 Carter Lane" to be considered a partial match when appropriate. The required quality of a match that is highlighted on the GUI may be adjustable by the user to avoid under or over inclusiveness. One of ordinary skill would understand that the methods of establishing a partial match above can be changed to any collection of appropriate algorithms that establish similarity between attributes. The embodiments are not limited in this regard.

Referring again to FIG. 2, all four source records 203a-d have a last name and birth date that match the reference identity record, so all values are highlighted in green or other color, shown in FIG. 2 as shaded areas 205. Three source records 203*a*, 203*c*, 203*d* also match gender, first name, and address fields with the reference identity record—the matching address is highlighted, for example, in green, shown in FIG. 2 as shaded areas 206. In this example, the address fields may show multiple addresses highlighted in green (shaded area 206) because the reference identity record may include multiple addresses for the same subject, for example. Two source records 203*a* and 203*c* also match middle name with the matching values highlighted in green or other color, shown in FIG. 2 as shaded areas 207. Source record 203*b* has a social security number that is partially matching with the reference identity record—the partial value is, for example, highlighted in yellow, shown in FIG. 2 as shaded area 208. In this example, two digits of the 9 digit number are transposed. In an embodiment, these values would be designated a partial match by an appropriate fuzzy matching algorithm, for example. The source record 203*b* has a first name value of "Buzz" (value 209) and source record 203*d* has a social security number value of 9 zeros (value 210). These values do not match any of the fields for the reference identity record, so it is not highlighted in green or yellow, or any other color, for example. Non-highlighted attribute values do not have a corresponding matching value within the reference identity record. One of ordinary skill would understand that the color coding schemes above can be changed to any appropriate color coding scheme. The embodiments are not limited in this regard.

After an identity is retrieved and viewed in the Workspace, a user can retrieve additional identities to display multiple identities on the screen at the same time. This is useful to view several identities that the user may want to link or unlink. A new identity may be retrieved using the same options as described above, for example, retrieve an identity by private ID, by source ID, or by demographics search, for example. In an embodiment, the new identity search results may be displayed in a new view, for example. A user may then select which records in the results to add to the workspace. The selected identity records can be added to the workspace using any number of well-known interface techniques. In an embodiment, a button is selected to combine the previous identity records with the newly selected identity records into one workspace view. Identity records may also be removed from the workspace view in a similar fashion.

A second way a user may use the index system is through task-based data stewardship. The GUI's task mode is used when a data steward (i.e., a user engaging in data stewardship tasks) wishes to view data stewardship tasks that were automatically detected and queued up by the index system. The data steward begins by viewing a list of all data stewardship tasks—the data steward can optionally search the task list to narrow down to a subset of tasks. Then the data steward selects a specific task from the list to view the task details.

Tasks are created when individual source records are posted to the index system. The posted source record, identified by the source ID and/or combination of source ID+native ID, for example, may be the 'trigger' record for a task. If the posted 'trigger' record meets the criteria for a data stewardship task, a task may be created and added to the task list, for example. The Source+Native ID of the 'trigger' record may be recorded in the task.

Figure 3:
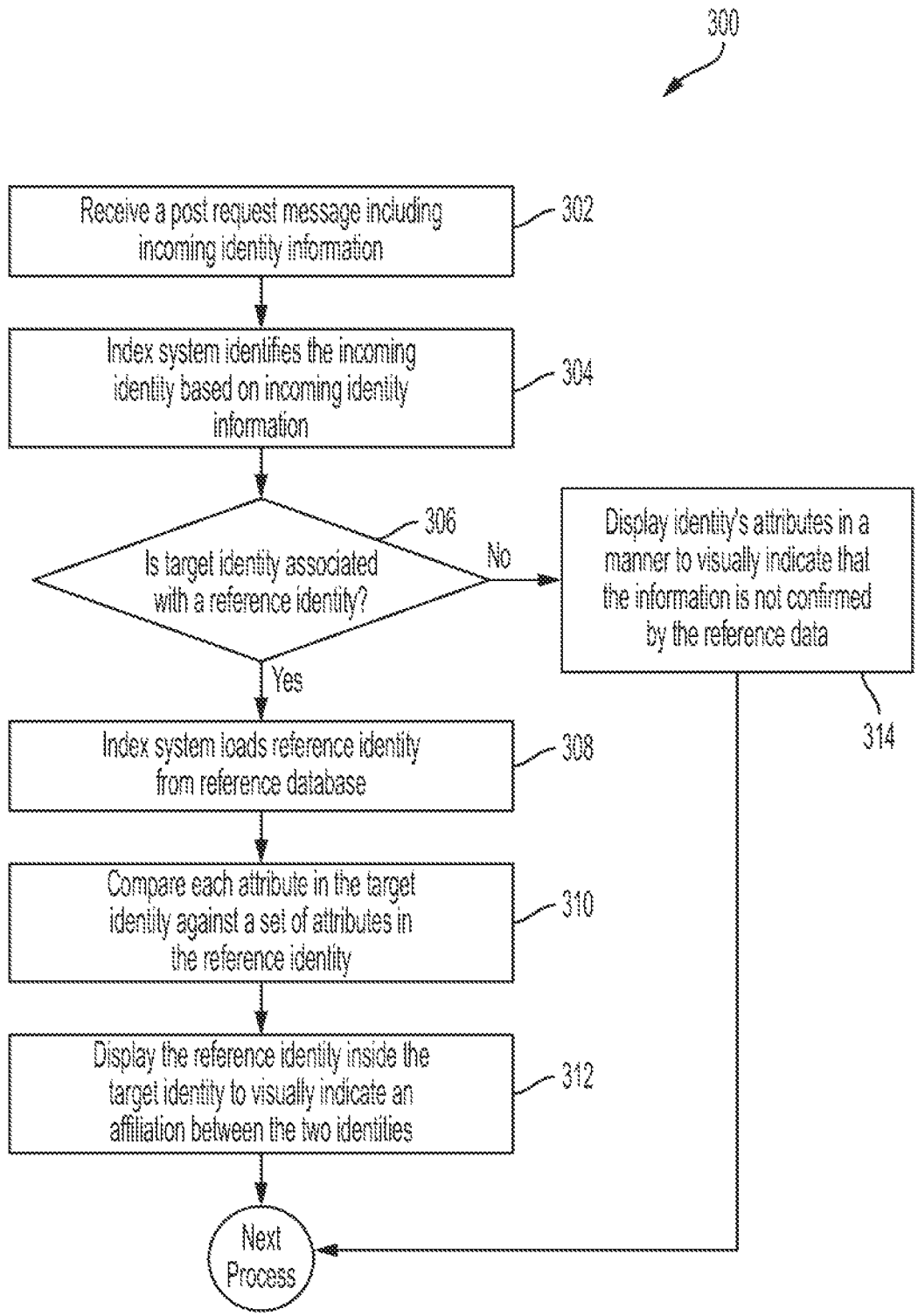
FIG. 3 is a flow diagram illustrating a method of regarding data stewardship tasks.

Referring to FIG. 3, an example method for using the system shown in FIG. 1 is provided. The example method of FIG. 3 may be practiced by the index system upon receipt of a request to post an incoming identity. In the method, a request message is received from, for example, a customer of the index system operator to post a new identity into the index system (step 302). The incoming identity information in the request message may be, for example, a customer ID and customer demographics attributes. The index system then identifies an incoming identity based on the incoming identity information and compares the incoming identity to the reference database to determine if there is a matching reference identity and persist this information along with the private identity in the private database. (step 304). From that point forward, any time a person uses the GUI to view the private identity, the index system first checks if a reference ID was stored along with the private identity (step 306). If a reference identity is found (step 306: Yes), the index system loads the reference identity attributes and information from the reference database (step 308). Multiple reference identities may be found during this comparison. Next, each attribute in the incoming identity and each reference identity are compared to determine the affiliation, if any, between the individual attributes of the incoming identity and any found reference identity (step 310). The reference identity and the incoming identity are then displayed to visually indicate the affiliation between the two identities (step 312). This comparison and affiliation is described in greater detail below in reference to FIG. 4. If no reference identity is found (step 306: No), the incoming identity's attributes are displayed in a manner to visually indicate that the incoming information is not confirmed by any reference data (step 314).

Figure 4:
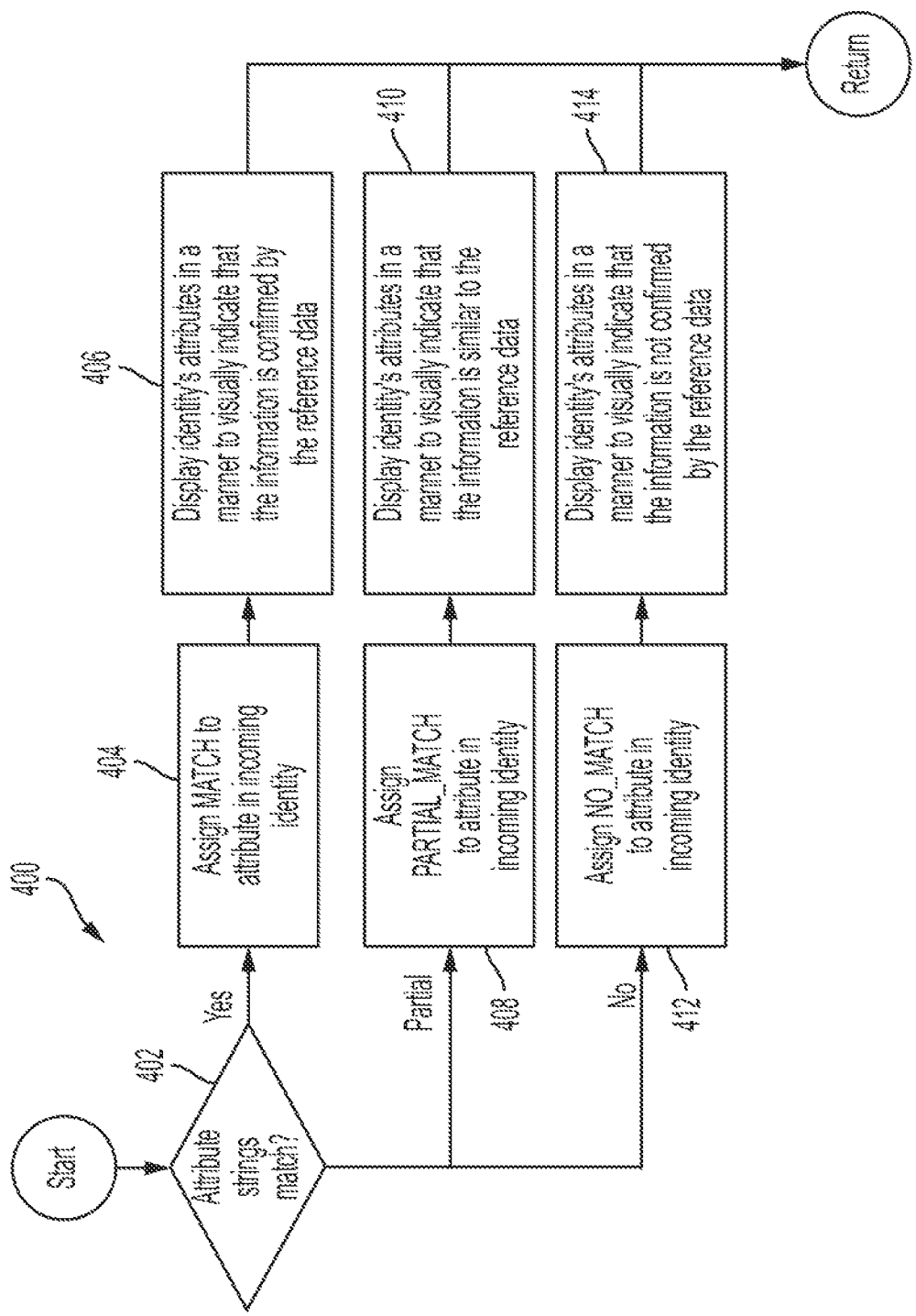
FIG. 4 is a flow diagram illustrating a method of regarding data stewardship tasks.

Referring to FIG. 4, a method of performing the comparison described above in reference to step 310 of FIG. 3 is provided. The method starts with a determination of whether the attribute string of the incoming identity matches any reference identity string for the corresponding attribute (step 402). There are three fundamental ways attributes can match. The attributes can be an actual match, meaning they are identical in both the incoming identity and the reference identity (step 402: Yes). In this case a "MATCH" tag may be assigned to the attribute in the incoming identity (step 404). The attribute that was matched is then displayed in a manner to visually indicate that information is confirmed by reference data, for example by displaying that attribute with a green color (step 406) as shown in FIG. 2. Alternatively, attributes can be a partial match, meaning at least some portion of the data in the attribute of the incoming data matches the reference data (step 402: Partial). In this case, a "PARTIAL_MATCH" is assigned to the attribute in the incoming identity (step 408). The attribute that was partially matched is then displayed in a manner to visually indicate that information is partially confirmed by reference data and is reliable but may require correction, for example by displaying that attribute with a yellow or orange color field (step 410) as shown in FIG. 2. Alternatively, attributes can have no match at all, meaning no portion of the data in the attribute of the incoming data matches the reference data (step 402: No). In this case, a "NO_MATCH" is assigned to the attribute in the incoming identity (step 412). The attribute that was not matched is then displayed in a manner to visually indicate that information was not confirmed by reference data and should be inspected for accuracy and a determination of whether the associated identity is a match, for example by displaying that attribute with no color field (step 414) as shown in FIG. 2.

Figure 5:
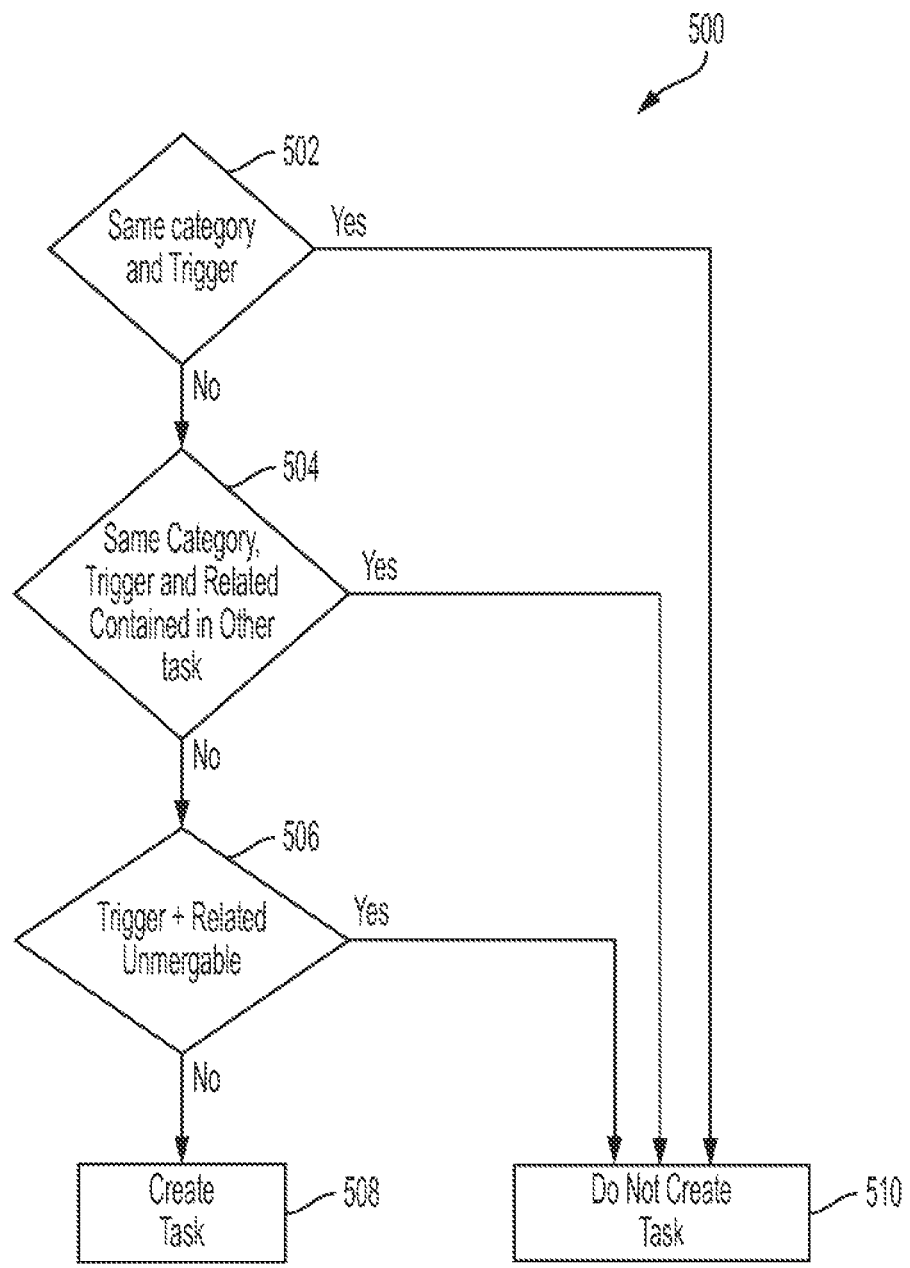
FIG. 5 is a flow diagram illustrating a method of regarding data stewardship tasks.

When creating data stewardship tasks, the index system takes steps to ensure that unnecessary or redundant data stewardship tasks are not created. Referring to FIG. 5, and following the example described above, when source record A:123 is posted and is a near match with source records A:456 and B:789, the index system creates a new data stewardship task. However, if the source record A:123 is posted again the next day (and it still is a near-match with A:456 and B:789) (502: Yes), the index system does not create a second, identical data stewardship task (510). The second task would be redundant, since the first task already captured the data event. The index system avoids creating redundant or unnecessary tasks in the following ways:

If, for example, a source record is posted to the index system and it is a near match to one or more other existing private identities, but a data stewardship task already exists between the posted source record and all the potentially-matching source records (504: Yes), the index system does not create a new data stewardship task (510).

If, for example, a source record is posted to index system and it is a near match to one or more other existing private identities, but a data stewardship task already exists between the posted source record and some of the potentially-matching source records, the index system updates the existing task (rather than creating a new one) to include all of the potentially-matching source records as of the most recent posting. This is a variation of (504: Yes) and a new data stewardship task is not created (510).

If, for example, a source record is posted to the index system and it is a near match to one or more other existing private identities, but a data stewardship task already exists between the posted source record and some or all of the potentially-matching source records but the records are not mergeable (506: Yes), a new data stewardship task is not created (510).

One of ordinary skill may recognize a number of other scenarios where creation of a new stewardship task is not desired. For example, only if the data record passes through all the above described scenarios, and any others that a person of ordinary skill would devise, (502/504/506: No) is a new data stewardship task created (508).

The intent of the behavior described above is to avoid creating additional tasks in the task list if an existing task (regardless of the task status) exists (or can be updated) that involves all the related source records. Otherwise, it would create redundant work for data stewards to resolve another task involving all the same records that the steward has already reviewed.

The task information may be based on the state of the index system data at the time the task was created. For example, suppose that a record from Source=A, Native ID=123 was posted on Jan. 4, 2019 at 10:31 am. At that point, the A:123 source record was a near match with an existing subject identity, which was assigned a private ID of 12f4, made up of source records A:456 and B:789. The matching algorithm score between the posted source record (A:123) and the existing subject identity was 0.762, for example. This is the information recorded for the data stewardship task (i.e., the trigger source record, the creation date time, the score, and so on). It is possible that subsequent updates to the A:123 source record or the B:789 source record could change the data-perhaps making the identities more similar with a higher match score, for example. This subsequent update would be visible to the data steward when they retrieve and view the task details, but it will not change the information associated with the original task. The original task will still record the score of 0.762 in this example.

The default Task List view may be a list of all data stewardship tasks that are not in a 'Closed' status. For example, each row in the list represents a single data stewardship task. Each task row includes several pieces of information:

The source+native ID of the 'trigger' source record which created the task.

The category, or type, of data stewardship task—current task categories are "Potential Match—Same Source" and "Potential Match—Cross Source".

The status of the task-possible task statuses are Open, In Progress, Deferred, and Closed.

The date and time the task was created.

The current user assigned to the task (if no user was assigned yet, each task starts out 'Unassigned').

The match algorithm score (a value between 0 and 1) detected at the time the task was created.

The Task List view may paginated, with each page showing a block of 100 tasks, for example. This ensures that the task list can be retrieved in an efficient manner without making the user wait too long for the full list to load. Each page, or block, of 100 tasks, for example, can be sorted by any of the column headings in the Task List view. Referring now to FIG. 6, an example task list is shown. In this example, the task list is paginated showing blocks of 50 tasks (note that not all tasks will be visible on the screen and that scrolling may be required to view all tasks in the displayed block). The task list includes several columns, including private ID 601; source ID 602; type 603; status 604; creation timestamp 605; assigned user 606; and match score 607.

The GUI also allows the data steward to search the task list to filter down to a smaller, more targeted subset of tasks depending on what is most important to the user. For example, a data steward may search for one or many specific sources. The source search input field may be a drop-down list that displays all the source IDs available in the index system. A data steward can select specific sources (one or many) by clicking next to the source name, for example. If the index system includes a very large number of sources, rather than scrolling through the list a user can type part of the source ID in the search box at the top of the source list. A data steward may also search for tasks with just a single category. The task category search input field is a drop-down list that displays all the available task categories. A data steward can select one or more task categories by clicking next to the task category in the list.

A data steward may also search for tasks with just a specific status (or statuses). The task status search input field is a drop-down list that displays all the available task statuses. A data steward can select one or more task statuses by clicking next to the task status in the list. By default, the task list does not display tasks of status "Closed". To view closed tasks, the data steward can select the "Closed" status from the task status search list.

A data steward may also search for tasks created within a range of dates. The task creation date search input field provides the user with a calendar widget-first select the beginning date for a date range, and then select another date (or the same date) for the end date of the date range. After selecting the beginning and end dates, the task list is filtered down to only those tasks created between the beginning and end dates.

A data steward may also search for tasks based on which user is currently assigned to the task (if any user is assigned). The task assignee search input field is a drop-down list that displays all the available users in the index system, for example. A data steward can select one or more users by clicking next to each user in the list. A data steward can also select 'Unassigned' to see tasks that are not yet assigned to any user.

A data steward may also search for tasks based on the matching algorithm score at the time the task was created. The matching algorithm score range runs from 0.0 to 1.0 (i.e., corresponding to a range of 0% to 100%). The threshold for determining when a data stewardship task is created may be adjusted by operators or data stewards. For example, most data stewardship tasks may be in the score range of 0.7 to 0.8 (i.e., between 70% and 80%). The task score search input fields are numeric fields, one for the lower end of the range and another for the upper end of the score range. A data steward can type a score value into the field, use the up/down arrows in the field to increment the score, or drag the circles on the 'slider' bar to adjust the score range.

A data steward may also search the task list using a combination of the search fields described above. This allows the data steward to narrow down to a very specific subset of tasks that might be most interesting to them. From the Task List view, a data steward can view the details of an individual task by clicking the task row in the Task List view.

After viewing one or more identities in the Workspace view or Task Detail view, a data steward may decide that the groupings of source records and Link IDs should be changed. The data steward may use GUI to make the changes they believe are appropriate. If the data steward believes two or more private IDs actually represent the same person, they can link the identities together into a single private ID using the user interface. If the data steward believes one or more source records do not belong with the other source records in a single private ID, they can unlink the source records using the user interface.

When two identities, each with a different private ID, are displayed at the same time in GUI, the data steward has the option to link those identities together. By linking the identities together, all source records from both identities will be combined into a single identity with a single private ID. One of the previous private IDs will become obsolete, and the remaining active private ID is the surviving private ID.

Figure 7B:
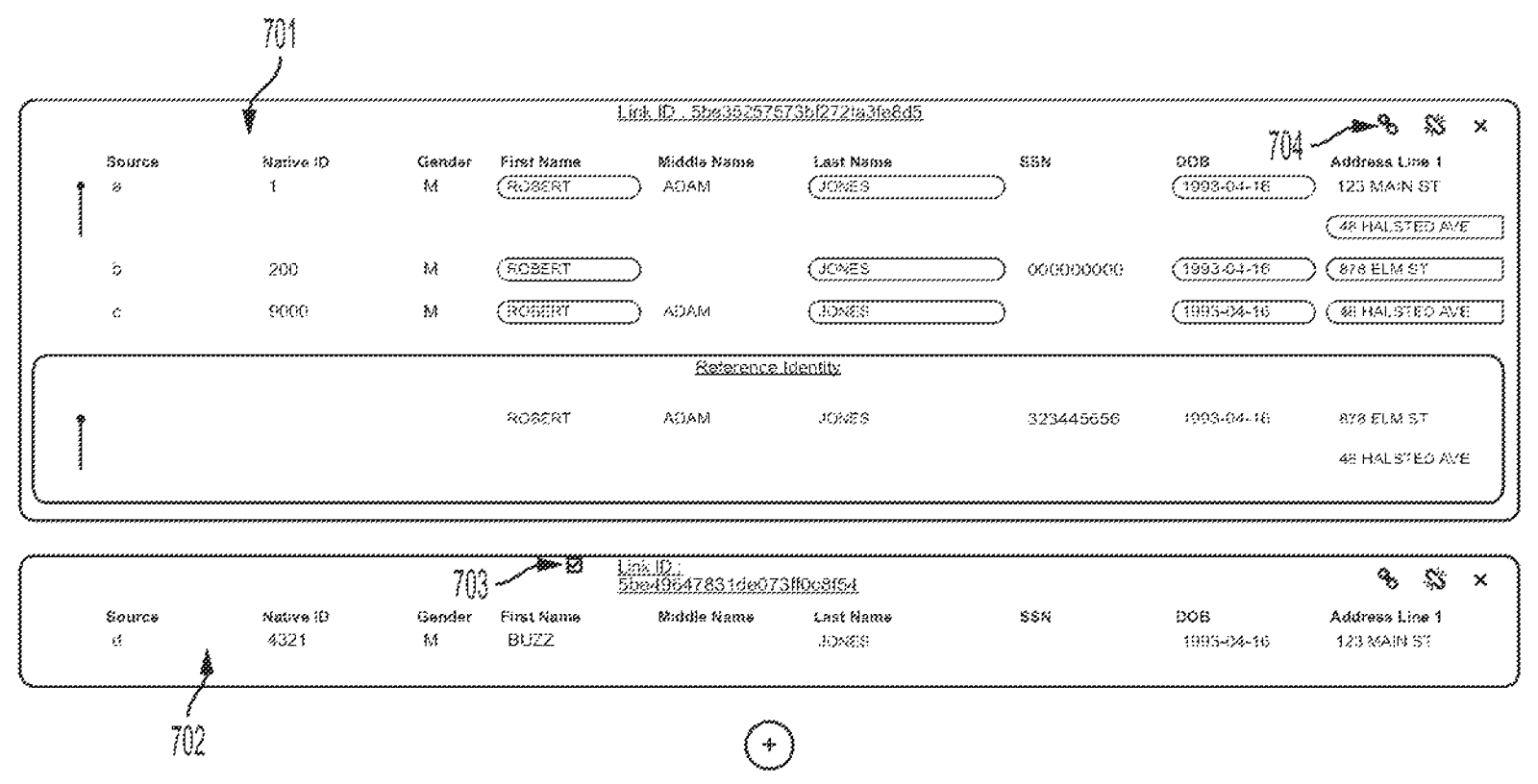
Figure 7C:
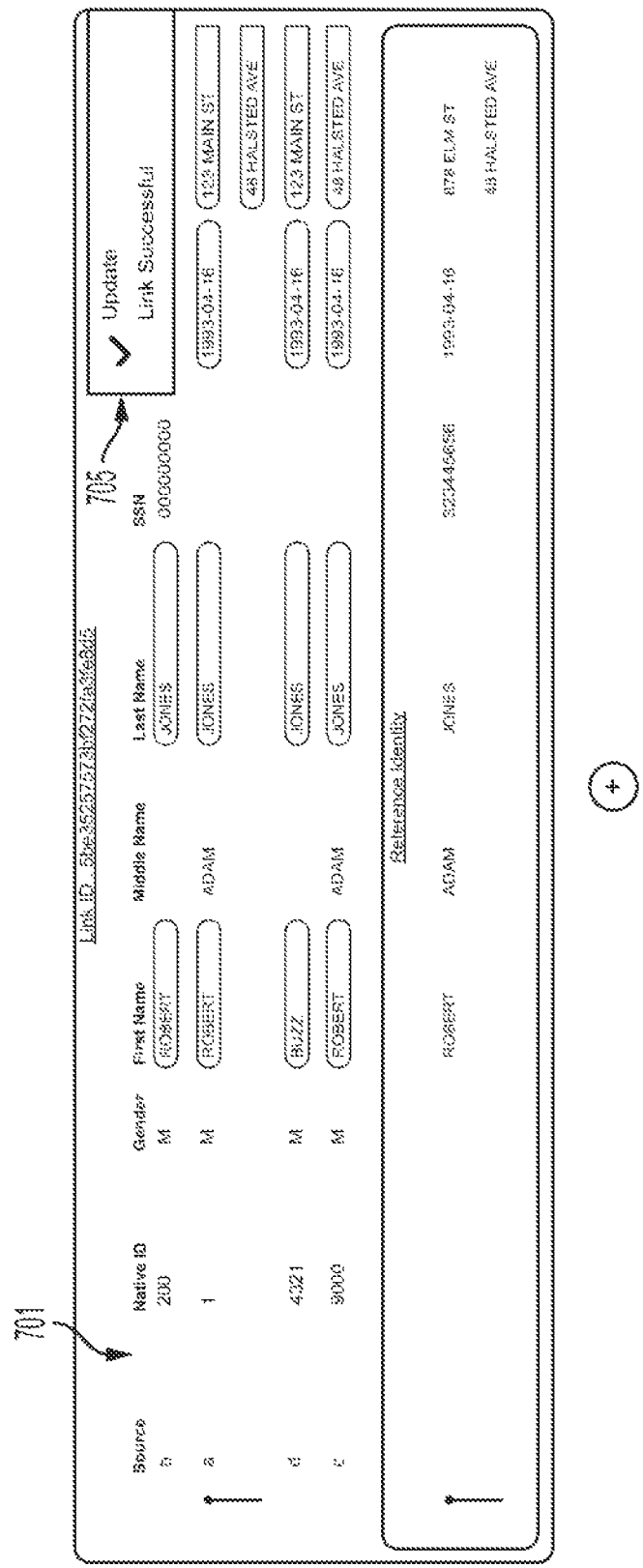

Referring to FIGS. 7A-7C, two identities are displayed in the Workspace view of the user interface. Referring to FIG. 7A, a first identity 701 and a second identity 702 are show. Each identity, in this example, has a set of action buttons in the upper right corner, but those action buttons are inactive. Referring now to FIG. 7B, the user selects the private ID that will become obsolete. In this example, a user may select the identity 702 by clicking to the left of the private ID. A checkbox 703 will appear with a check mark to indicate you have selected the private ID 702. When a user has selected the identity 702, an action button 704 will also become active in the private ID 701—the action button 704 that is now active is the 'Link' action button, which, in this example, is a blue icon that looks like two links in a chain. In the example shown in FIG. 7B, where the lower identity 702 is selected, and the 'Link' action button 704 is active in the upper identity 702. To link the selected (obsolete) private ID 702 and its source records into the surviving identity 701, click the 'Link' action button 704 in the surviving identity 701. Whichever identity for which a user clicks the 'Link' button will be the surviving identity, and its private ID remains active. In the example of FIG. 7C, after clicking the 'Link' action button 704, a green banner 705 briefly appears in the upper right corner indicating that the link action was successful. The source records from the obsolete private ID are combined with the source records of the surviving private ID 701, and all the combined source records are now shown grouped together in the surviving private ID 701.

In some cases, a data steward may want to link more than two identities together. The linking operation described above applies to a set of two identities at a time-one identity is selected as the obsolete identity, and that identity's source records are combined into the surviving identity by clicking the 'Link' action button in the surviving identity. To combine three or more identities, a data steward starts by combining two identities, and then repeats the process until all the obsolete identities have been combined into a single surviving identity. When a data steward selects an identity to become linked into a surviving identity, the 'Link' action button will become active in all the other identities on the screen, but the selected identity is only linked into the one identity in which a data steward actually clicks the 'Link' action button. The data steward controls which identity is the surviving identity by deciding which identity in which to click the 'Link' action button.

When one (or more) identities are displayed at the same time in the GUI, the data steward also has the option to unlink source records from an identity. By unlinking one or more source records, the data steward is asserting that the unlinked source record(s) are a different person than the rest of the identity to which they originally belonged. The unlinked source record(s) are moved into a new private ID. If more than one source record is selected from an identity, then all the selected source records are unlinked together, and they remain together in the new private ID to which they are assigned. All source records which were NOT selected during the unlink operation remain in the original private ID.

As described above, the index system GUI allows a data steward to link identities together and unlink source records from a single identity. At times, a data steward may need to make more complicated decisions that involve combinations of linking and unlinking across several identities. To perform these more complicated actions, the data steward can use the linking and unlinking actions in steps to accomplish his or her final goal.

As an example, suppose a data steward is viewing two identities in the GUI. The first identity is made up of several source records—one of the source records is for a person named 'Jack Smith', and all the other source records are for a person named 'John Smith'. The second identity is also made up of several source records-one of the source records is for a person named 'Jack Smith', and all the other source records are for a person named 'James Smith'. The data steward decides that there are three distinct people represented in the data—The first identity represents John Smith, the second identity represents James Smith (a different person), and there is a third person, Jack Smith, who has source records in each of the first two identities.

The final outcome desired by the data steward may be, for example, to have both of the 'Jack Smith' source records unlinked from their current identities and combined together into a third private ID. To accomplish this, the data steward first unlinks the one 'Jack Smith' source record from the 'John Smith' identity. Next, the data steward unlinks the one 'Jack Smith' source record from the 'James Smith' identity. At this point, there are four identities (and four Link IDs) displayed-one for the original 'John Smith' identity; one for the original 'James Smith' identity; and two for each of the 'Jack Smith' source records that were individually unlinked. The last step is for the data steward to link together the two 'Jack Smith' identities into a single identity. The data steward has taken three steps (two unlink steps followed by a single link step) to arrive at their desired final outcome, using the building blocks of linking identities and unlinking source records. A person of ordinary skill will understand that the precise details on the user interface for performing linking and unlinking operations may be changed in accordance with various methods and standards known in the art. For example, instead of a select and link method described above using a link button as shown and described in reference to FIGS. 7A-7C, the interface could use a "drag and drop" feature or any other method for grouping and ungrouping interface items at will to be confirmed, for example, with an "apply" button. Threshold checks may also be performed upon clicking of the "apply" button and a confirmation or warning may be displayed to the data steward if the new groupings are below a pre-set and/or adjustable threshold. The embodiments are not limited in this regard.

The steps to link or unlink source records described in above apply in both the Workspace view (part of Search Mode) and the Task Details view (part of Task Mode). In the Workspace view, the user has simply retrieved one or more identities and made link/unlink decisions independent of any index system-detected data stewardship task. In the Task Details view, there are additional aspects of the data stewardship task that can be updated by the user both before and after the user is finished with any linking or unlinking actions they choose to make.

The task status can be updated in the Task Details view. The task status may be displayed near the top of the Task Details view. If a data steward clicks on the task status field, a drop-down list may appear showing the available task status values. If a data steward selects a different task status value from the list and clicks (or tab out of the field), the task may be automatically updated with the new task status. By changing the task status to 'Closed', the task may be not removed or deleted, but it may not appear any longer in the default Task List view (the default Task List view shows tasks in any status other than 'Closed'). Closed tasks can still be retrieved in the Task List view by searching for the specific task status of 'Closed' (described in section 4 of this document). Task statuses of 'Deferred' or 'In Progress' can be useful to track tasks that a user might leave in a partially-reviewed state for an indefinite period of time.

Figure 8A:
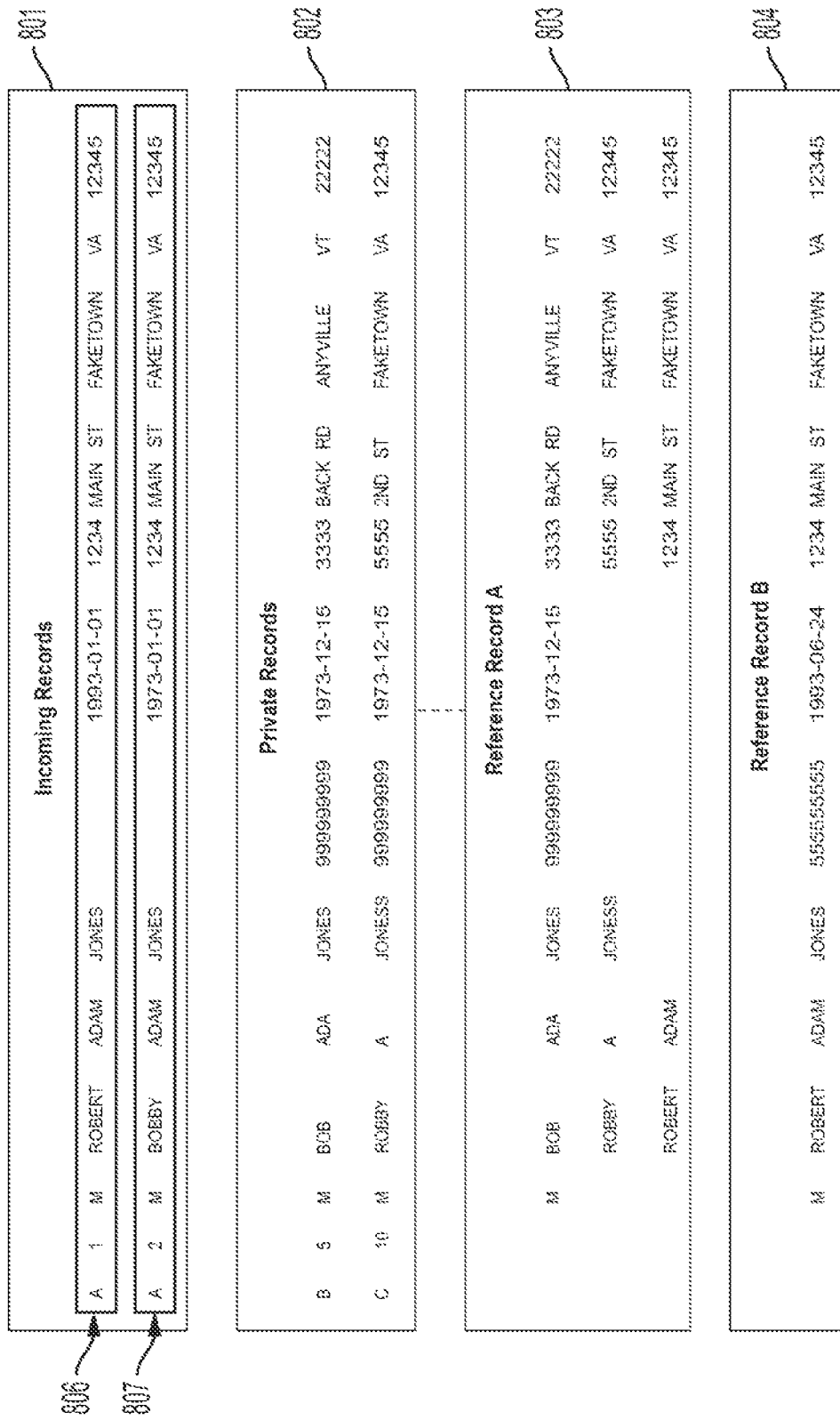
FIGS. 8A-8B are an example graphical user interface for use in implementing the disclosed embodiments.
Figure 8B:
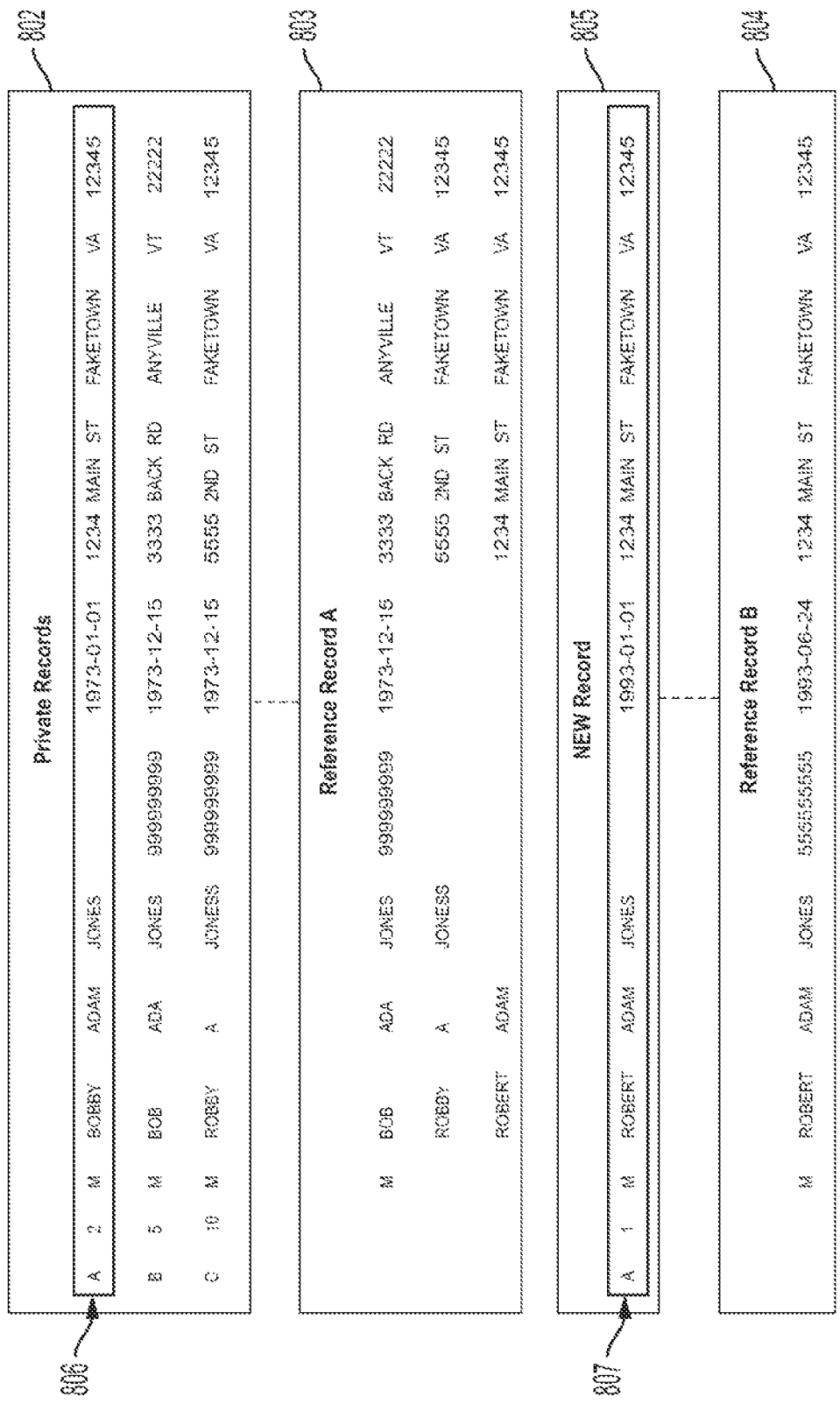

In an embodiment, source records may be analyzed by the index system to determine which, if any, existing identities and/or proposed new identities that the new source records may belong to, as well as any existing reference identities that any proposed new identities should be associated with. The suggested associations generated by this analysis will be applied to the output view. The analysis and output view can be applied to any set of source records that the user would like to view in the interface, regardless of whether the records are included in a task or manually loaded by the user. The interface may provide user adjustable weights and/or thresholds with regard to the parameters of the analyzing algorithm so that the user can tune the suggested associations. The automatic associations along with the customizable weights and/or thresholds may increase a user's efficiency by reducing manual effort when determining what operations need to be applied to the set of source records in the current view. For example, in FIG. 8A, an example task is shown having incoming records 801 comprising record A1 806 and record A2 807. Using the attributes of records 806 and 807, the index system identified existing private records 802 associated with the same private subject identity, existing reference identity 803 associated with reference subject identity A, and reference identity 804 associated with reference subject identity B. Using user adjustable weights or thresholds with regard to each of the attributes in the incoming records 801, for example date of birth, the index system may automatically associate records 806 and 807 with one or more of the identity records identified by the index system as being potentially relevant to the task. For example, as shown in FIG. 8B, record 806 is associated with private record 802 and record 807 is associated with new record 805. Using the interface described above in reference to FIGS. 7A-7C or other interface method within ordinary skill (i.e., drag-and-drop with "apply" button), a user may be given the option to confirm the associates of records 806, 807 with a "one click" button or other interface feature well known to those of ordinary skill. In the event that the user wishes to establish a different association, the thresholds may be adjusted or records may be selected and linked or unlinked as discussed above.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. An improved system for viewing and performing data stewardship tasks using a reference database, the system comprising:
   a private data system that includes a private processor and a private database, wherein the private data system is capable of accessing a reference data system that includes a reference database containing a plurality of reference identity data records that only contain identity data attributes that are used for resolving and verifying identities of unknown data records that are external to the reference data system;
   a display configured to display a data stewardship task based on one or more identity data attributes received from the reference database, wherein the displayed data stewardship task indicates a match quality for each of the one or more received identity data attributes and one or more saved identity data attributes contained within one of a plurality of saved data records stored in the private database; and
   a graphical user interface programmed to receive a first user input indicating one of a linking action or an unlinking action and which results in at least one of a prevention of duplication of data and a correction of incorrect or duplicated data.

2. The system of claim 1, wherein the data stewardship task is created by configuring the processor to:
   receive, at the private data system, a data record comprising identity information having a set of received identity data attributes representing an identity of a subject;
   send, by the private data system, the identity information to the reference data system to verify the identity of the subject;
   receive, from the reference data system, a return message including a set of combined identity data attributes representing a verified subject and comprising the set of received identity data attributes and one or more reference identity data attributes representing a selected reference subject, wherein the return message verifies the identity of the subject to the private database and establishes to the private database that the subject, the selected reference subject, and the verified subject are all the same subject;

compare the one or more combined identity data attributes to the one or more saved identity data attributes contained within the plurality of saved data records in the private database; and on a condition that the received data record is a near match to one or more of the plurality of saved data records in the private database that is not contained within a currently existing data stewardship task, create a data stewardship task record that contains the one or more combined identity data attributes and the one or more saved identity data attributes of each of the plurality of saved data records that are near matches to the received data record.

3. The system of claim 2, on a condition that the received data record is a near match to a single existing private data record in the private database above a threshold for creating the data stewardship task, the private data system is further configured to:

assign a new private identifier to the received data record save the received data record as a new private data record, and link the new private data record with the single existing private data record such that both data records represent the same subject.

4. The system of claim 1, wherein each private data record in the private database pertains to a unique private subject and is comprised of one or more private identity data attributes representing the unique private subject, wherein one of such private identity data attributes for each private data record is a private record identifier (ID) attribute.

5. The system of claim 1, wherein each reference data record in the reference database pertains to a unique reference subject and is comprised of one or more reference identity data attributes representing the unique reference subject, wherein one of such reference identity data attributes for each reference data record is a reference record ID attribute.

6. The system of claim 1, wherein the first user input indicates the linking action and wherein the first user input includes a reference to an identified saved private data record included in the data stewardship task, and wherein the private data system is further configured to prevent duplication of data by assigning the received data record a private record ID of the identified saved private data record.

7. The system of claim 1, wherein the first user input indicates the unlinking action and wherein the first user input includes a reference to an identified saved private data record included in the data stewardship task, and wherein the private data system is further configured to prevent the incorrection of data by assigning the identified saved private data record a new private identifier and saving the identified saved private data record as a new private data record.

8. The system of claim 1 on a condition that the received data record is not a near match to any of the plurality of saved private data records in the private database the private data system is further configured to assign a new private identifier to the received data record and saving the received data record as a new private data record.

9. The system of claim 1, wherein, prior to creating the data stewardship task, the private data system is further configured to, on a condition that a currently existing data stewardship task contains a previously received data record is a near match to the one or more of the plurality of saved private data records in the private database, merge the received data record into the currently existing data stewardship task.

10. The system of claim 1, wherein the match quality is indicated using a color coding scheme that uses a unique color, lack of color, or other visual cues to indicate one of a match, a partial match, and no match.

11. An improved method for creating data stewardship tasks using a reference database, the method comprising:

receiving, from a reference database, a message including a set of combined identity data attributes representing a verified subject and comprising a set of received identity data record attributes of a received data record representing an identity of a subject and one or more reference identity data attributes representing a selected reference subject, wherein the message verifies the identity of the subject to a private database and establishes to the private database that the subject, the selected reference subject, and the verified subject are all the same subject, wherein the reference database contains a plurality of identity data records that only contain identity attributes that are used for resolving and verifying identities of unknown data records that are external to the reference database;

comparing the one or more combined identity data attributes to a plurality of saved private data records, wherein each saved private data record comprises one or more saved private identity data attributes;

on a condition that the received data record is a near match to one or more of the plurality of saved private data records, creating a data stewardship task record that contains the one or more combined identity data attributes and the one or more saved private identity data record attributes of each of the plurality of saved private data records that are near matches to the received data record;

displaying a data stewardship task on a display if the data stewardship task was created using either the private database or the reference database, wherein the displayed data stewardship task indicates a match quality for each of the one or more received identity data attributes and the one or more saved private identity data attributes; and receiving a first user input indicating one of a linking action or an unlinking action and which results in at least one of a prevention of duplication of data and a correction of incorrect or duplicated data.

12. The method of claim 11 further comprising, prior to receiving message including a set of combined identity data attributes, receiving, from an external data system, the received data record comprising a set of received identity data attributes.

13. The method of claim 11 further comprising, prior to receiving message including a set of combined identity data attributes, sending the set of received identity data record attributes to a reference database to verify the identity of the subject.

14. The method of claim 11, wherein the first user input indicates the linking action and wherein the first user input includes a reference to an identified saved private data record included in the data stewardship task, the method further comprising preventing duplication of data by assigning the received data record a private record identifier of the identified saved private data record.

15. The method of claim 11, wherein the first user input indicates the unlinking action and wherein the first user input includes a reference to an identified saved private data record included in the data stewardship task, the method further comprising preventing the incorrection of data by assigning the identified saved private data record a new private identifier and saving the identified saved private data record as a new private data record.

16. The method of claim 11 further comprising, on a condition that the received data record is not a near match to any of the plurality of saved private data records, assigning a new private identifier to the received data record and saving the received data record as a new private data record.

17. The method of claim 11 further comprising, prior to creating the data stewardship task, on a condition that a currently existing data stewardship task contains a previously received data record is a near match to the one or more of the plurality of saved private data records, merging the received data record into the currently existing data stewardship task.

18. The method of claim 11, wherein the match quality is indicated using a color coding scheme that uses a unique color, lack of color, or other visual cues to indicate one of a match, a partial match, and no match.

19. The method of claim 11, wherein the displayed data stewardship task indicates the match quality for each of the one or more received identity data attributes and the one or more saved private identity data attributes.

20. The method of claim 11, wherein the data stewardship task record also contains one or more saved private identity data attributes of each of the plurality of saved private data records that are near matches to the received data record.

21. The method of claim 11 further comprising, on a condition that the received data record is a match to a single existing private data record in the private database above a threshold for creating the data stewardship task:
   assigning a new private identifier to the received data record;
   saving the received data record as a new private data record; and
   linking the new private data record with the single existing private data record such that both data records represent the same subject.

* * * * *

UNITED STATES PATENT AND TRADEMARK OFFICE
CERTIFICATE OF CORRECTION

PATENT NO. : 12,210,498 B1  
APPLICATION NO. : 18/393926  
DATED : January 28, 2025  
INVENTOR(S) : Jonathan Paul Case et al.

Page 1 of 1

It is certified that error appears in the above-identified patent and that said Letters Patent is hereby corrected as shown below:

On the Title Page

Change title from "SYSTEM AND METHOD FOR AUTOMATED CLUSTERING OF SUBJECT DATA" to "METHODS AND SYSTEMS FOR FACILITATING DATA STEWARDSHIP TASKS"

In the Specification

Column 1, Lines 1-2, Change title from "SYSTEM AND METHOD FOR AUTOMATED CLUSTERING OF SUBJECT DATA" to "METHODS AND SYSTEMS FOR FACILITATING DATA STEWARDSHIP TASKS"

Signed and Sealed this  
Twenty-fifth Day of November, 2025

John A. Squires  
*Director of the United States Patent and Trademark Office*